United States Patent
Farrugia et al.

(10) Patent No.: US 9,877,485 B2
(45) Date of Patent: *Jan. 30, 2018

(54) SILVER POLYESTER-SULFONATED NANOPARTICLE COMPOSITE FILAMENTS AND METHODS OF MAKING THE SAME

(71) Applicant: XEROX CORPORATION, Norwalk, CT (US)

(72) Inventors: Valerie M. Farrugia, Oakville (CA); Barkev Keoshkerian, Thornhill (CA); Michelle N. Chrétien, Mississauga (CA)

(73) Assignee: XEROX CORPORATION, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,255

(22) Filed: Apr. 13, 2016

(65) Prior Publication Data

US 2017/0295795 A1 Oct. 19, 2017

(51) Int. Cl.

| A01N 55/02 | (2006.01) |
|---|---|
| C08K 3/08 | (2006.01) |
| A01N 59/16 | (2006.01) |
| C09D 5/14 | (2006.01) |
| C09D 7/12 | (2006.01) |
| C09D 167/00 | (2006.01) |

(52) U.S. Cl.
CPC ............ *A01N 59/16* (2013.01); *A01N 55/02* (2013.01); *C08K 3/08* (2013.01); *C09D 5/14* (2013.01); *C09D 7/1216* (2013.01); *C09D 167/00* (2013.01); *C08K 2003/0806* (2013.01)

(58) Field of Classification Search
None
See application file for complete search history.

(56) References Cited

U.S. PATENT DOCUMENTS

| 2,285,552 A | 6/1942 | Alfthan |
|---|---|---|
| 3,046,178 A | 7/1962 | Tupper |
| 4,012,557 A | 3/1977 | Cornelis |
| 4,749,347 A | 6/1988 | Valavaara |
| 4,913,864 A | 4/1990 | Soga et al. |
| 5,121,329 A | 6/1992 | Crump |
| 5,303,141 A | 4/1994 | Batchelder et al. |
| 5,340,433 A | 8/1994 | Crump |
| 5,348,832 A | 9/1994 | Sacripante et al. |
| 5,402,351 A | 3/1995 | Batchelder et al. |
| 5,503,785 A | 4/1996 | Crump et al. |
| 5,587,913 A | 12/1996 | Abrams et al. |
| 5,593,807 A | 1/1997 | Sacripante et al. |
| 5,604,076 A | 2/1997 | Patel et al. |
| 5,648,193 A | 7/1997 | Patel et al. |
| 5,658,704 A | 8/1997 | Patel et al. |
| 5,738,817 A | 4/1998 | Danforth et al. |
| 5,764,521 A | 6/1998 | Batchelder et al. |
| 5,840,462 A | 11/1998 | Foucher et al. |
| 5,853,944 A | 12/1998 | Foucher et al. |
| 5,916,725 A | 6/1999 | Patel et al. |
| 5,919,595 A | 7/1999 | Mychajlowskij et al. |
| 5,939,008 A | 8/1999 | Comb et al. |
| 5,945,245 A | 8/1999 | Mychajlowskij et al. |
| 6,017,671 A | 1/2000 | Sacripante et al. |
| 6,020,101 A | 2/2000 | Sacripante et al. |
| 6,054,240 A | 4/2000 | Julien et al. |
| 6,140,003 A | 10/2000 | Sacripante et al. |
| 6,143,457 A | 11/2000 | Carlini et al. |
| 6,210,853 B1 | 4/2001 | Patel et al. |
| 6,730,252 B1 | 5/2004 | Teoh et al. |
| 6,866,807 B2 | 3/2005 | Comb et al. |
| 6,923,634 B2 | 8/2005 | Swanson et al. |
| 7,312,011 B2 | 12/2007 | Patel et al. |
| 9,243,141 B1 | 1/2016 | Farrugia et al. |
| 2004/0222561 A1 | 11/2004 | Hopkins |
| 2012/0202148 A1 | 8/2012 | Veregin et al. |
| 2015/0084222 A1 | 3/2015 | Heston et al. |
| 2015/0290280 A1 | 10/2015 | Petrak et al. |
| 2015/0328835 A1 | 11/2015 | Wu et al. |

OTHER PUBLICATIONS

Kundu et al., "Micelle bound redox dye marker for nanogram level arsenic detection promoted by nanoparticles," New J. Chem., 2002, 26, 1081-1084.
Mukherjee et al., "Potential Theranostics Application of Bio-Synthesized Silver Nanoparticles (4-in-1 System)," Theranostics 2014; 4(3):316-335.
Ghosh, S.K. et al., "Silver and Gold Nanocluster Catalyzed Reduction of Methylene Bloue by Arsine in a Micellar Medium", Langmuir. 18(23):8756-8760 (2002).
Tsavalas. J.G. et al., "Grafting Mechanisms in Hybrid Miniemulsion Polymerization", J. Appl. Polym. Sci., 87:1825-1836 (2003) 1-1.
Rashid et al., "Synthesis of Silver Nano Particles (Ag-NPs) and their uses for Quantitative Analysis of Vitamin C Tablets", J. Pharm. Sci. 12(1):29-33 (2013).

*Primary Examiner* — Gina Justice
(74) *Attorney, Agent, or Firm* — Pillsbury Winthrop Shaw Pittman LLP

(57) ABSTRACT

A composite filament includes a sulfonated polyester matrix and a plurality of silver nanoparticles dispersed within the matrix and methods of making thereof. Various articles can be manufactured from such composite filaments.

20 Claims, 3 Drawing Sheets

SILVER POLYESTER-SULFONATED NANOPARTICLE COMPOSITE FILAMENTS AND METHODS OF MAKING THE SAME

CROSS-REFERENCE TO RELATED APPLICATIONS

Reference is made to commonly owned and co-pending, U.S. patent application Ser. No. 15/098,270 (not yet assigned) entitled "SILVER NANOPARTICLE-SULFONATED POLYESTER COMPOSITE POWDERS AND METHODS OF MAKING THE SAME" to Valerie M. Farrugia et al., electronically filed on the same day herewith, the entire disclosures of which are incorporated herein by reference in its entirety.

BACKGROUND

The present disclosure relates to composites comprising metal nanoparticles dispersed throughout the composite matrix for use in Fused Deposition Modelling (FDM).

The medical community's reliance on three dimensional 3D printing for various applications is rapidly increasing and covers areas such as tissue and organ fabrication, customizable devices such as prosthetics, mouth guards, orthotics, hearing aids and implants, and pharmaceutical exploration related to controlled drug delivery and personalized drug production. Many of these medical applications require composite material that can inhibit bacterial, microbial, viral or fungal growth. Other products for 3D printing such as kitchen tools, toys, education materials and countless household items also provide a favorable environment for bacteria growth, and therefore antibacterial composite materials are also desirable for use in connection with these products. Due to the layered construction of 3D printed material, the potential for bacterial growth can be very significant, especially since certain bacterial strains can actually thrive within the detailed structural make-up of these materials. Washing alone does not completely sterilize the surfaces and crevasses of these products.

Therefore, there exists a need for new materials with antibacterial properties for 3D printing. One of the 3D printing methods is FDM, which is a common additive manufacturing (3D printing) technique. FDM is an additive layer manufacture technology for fabricating physical, 3D objects from computer-aided-design (CAD) models. FDM technology can process common 3D printing materials, such as, polylactic acid (PLA), acrylonitrile butadiene styrene (ABS), and high-density polyethylene (HDPE). FDM operates on the principle of heating and then extruding a feedstock material, typically as a series of stacked, patterned layers, thereby to form a build. FDM process employs molten thermoplastic/polymers as build materials for making 3D articles via the extrusion of the molten plastics. This modelling process is a multi-step approach where a computer-aided design is rendered, in the case of medical applications this model would come from an ultrasound, computed tomography scan or magnetic resonance image. This design is then processed by software which sets the desired build parameters. The file data is used by the FDM apparatus to build the article. The spool of filament material is fed into a headed extrusion head which delivers the semi-liquid material onto the build platform in a layer-by-layer fashion. As the model is built, the layers solidify upon deposition due to the temperature differential of the build chamber. In some cases the head can also extrude a removable support material which acts as a scaffold to hold the article layers in place as it cools. This support material can later be removed via heating, breaking off or washing (in ultrasonic vibration tank). A layer by layer method of depositing materials for building a model is described in U.S. Pat. No. 5,121,329 which is incorporated herein by reference. Examples of apparatus and methods for making three-dimensional models by depositing layers of flowable modeling material are described in U.S. Pat. No. 4,749,347, U.S. Pat. No. 5,121,329, U.S. Pat. No. 5,303,141, U.S. Pat. No. 5,340,433, U.S. Pat. No. 5,402,351, U.S. Pat. No. 5,503,785, U.S. Pat. No. 5,587,913, U.S. Pat. No. 5,738,817, U.S. Pat. No. 5,764,521 and U.S. Pat. No. 5,939,008. An extrusion head extrudes heated, flowable modeling material from a nozzle onto a base. The base comprises a modeling substrate which is removably affixed to a modeling platform. The extruded material is deposited layer-by-layer in areas defined from the CAD model, as the extrusion head and the base are moved relative to each other in three dimensions by an x-y-z gantry system. The material solidifies after it is deposited to form a three-dimensional model. It is disclosed that a thermoplastic material may be used as the modeling material, and the material may be solidified after deposition by cooling.

SUMMARY

In some aspects, embodiments herein relate to filament composites comprising a sulfonated polyester matrix and a plurality of silver nanoparticles dispersed within the matrix for use in Fused Deposition Modelling (FDM) application.

In some aspects, embodiments herein relate to method comprising heating a sulfonated polyester resin in an organic-free solvent; adding a solution of silver (I) ion to the heated resin in the organic-free solvent to form a mixture; adding a solution of a reducing agent to the mixture, thereby forming an emulsion of particles comprising a sulfonated polyester matrix and a plurality of silver nanoparticles disposed within the sulfonated polyester matrix; aggregating the emulsion of particles to form aggregated particles; coalescing the aggregated particles to form coalesced particles; washing the coalesced particles, thereby forming a composite powder; and extruding the composite powder to produce the composite filament.

In some aspects, embodiments herein relate to articles comprising a composite powder comprising a sulfonated polyester matrix and a plurality of silver nanoparticles dispersed within the matrix, wherein the silver nanoparticle is present in the composite filament in a range from about 0.5 ppm to about 50,000 ppm; and further wherein the composite filament has a diameter of from about 0.5 mm to about 5 mm.

BRIEF DESCRIPTION OF DRAWINGS

Various embodiments of the present disclosure will be described herein below with reference to the figures wherein.

DETAILED DESCRIPTION

Figure 1:
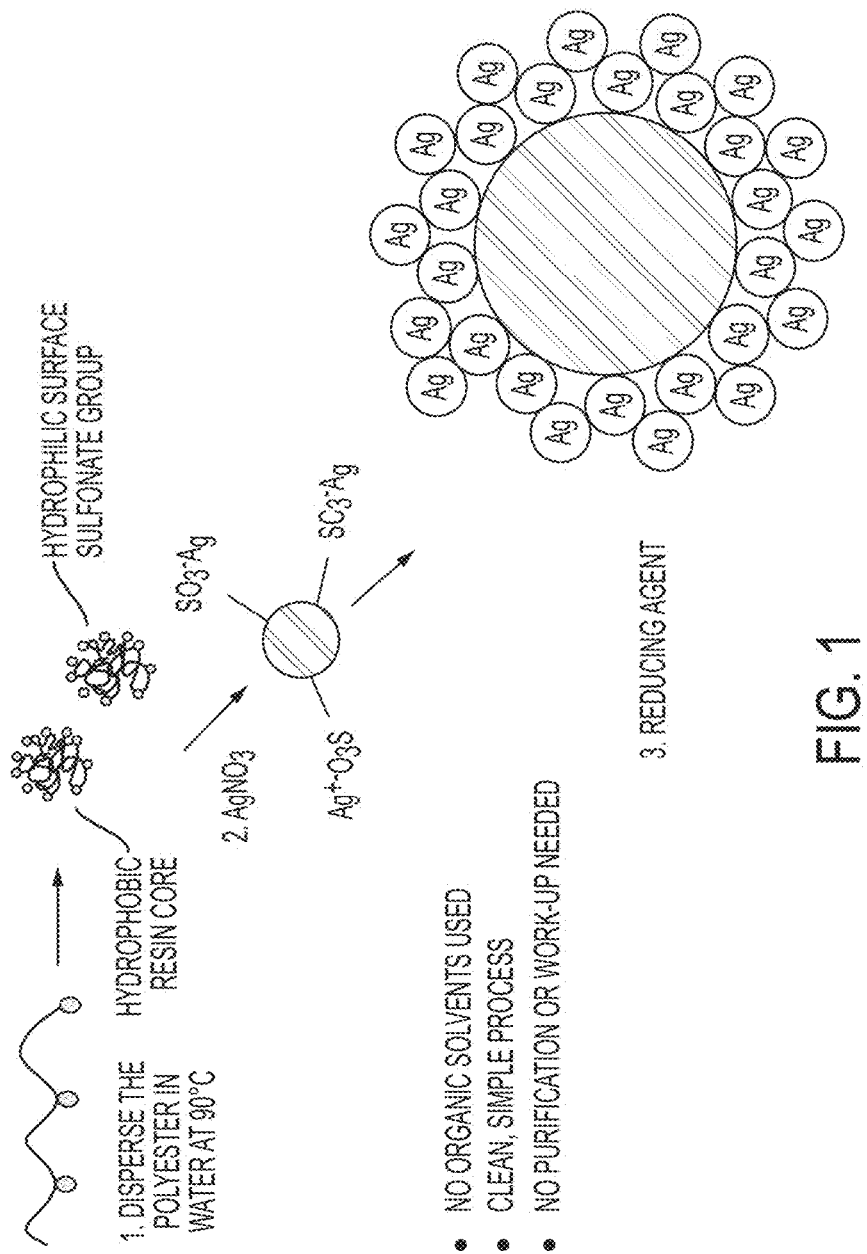
FIG. 1 shows a schematic of a possible mechanism of sodio sulfonated polyester self-assembly in the presence of Ag.
Figure 2:
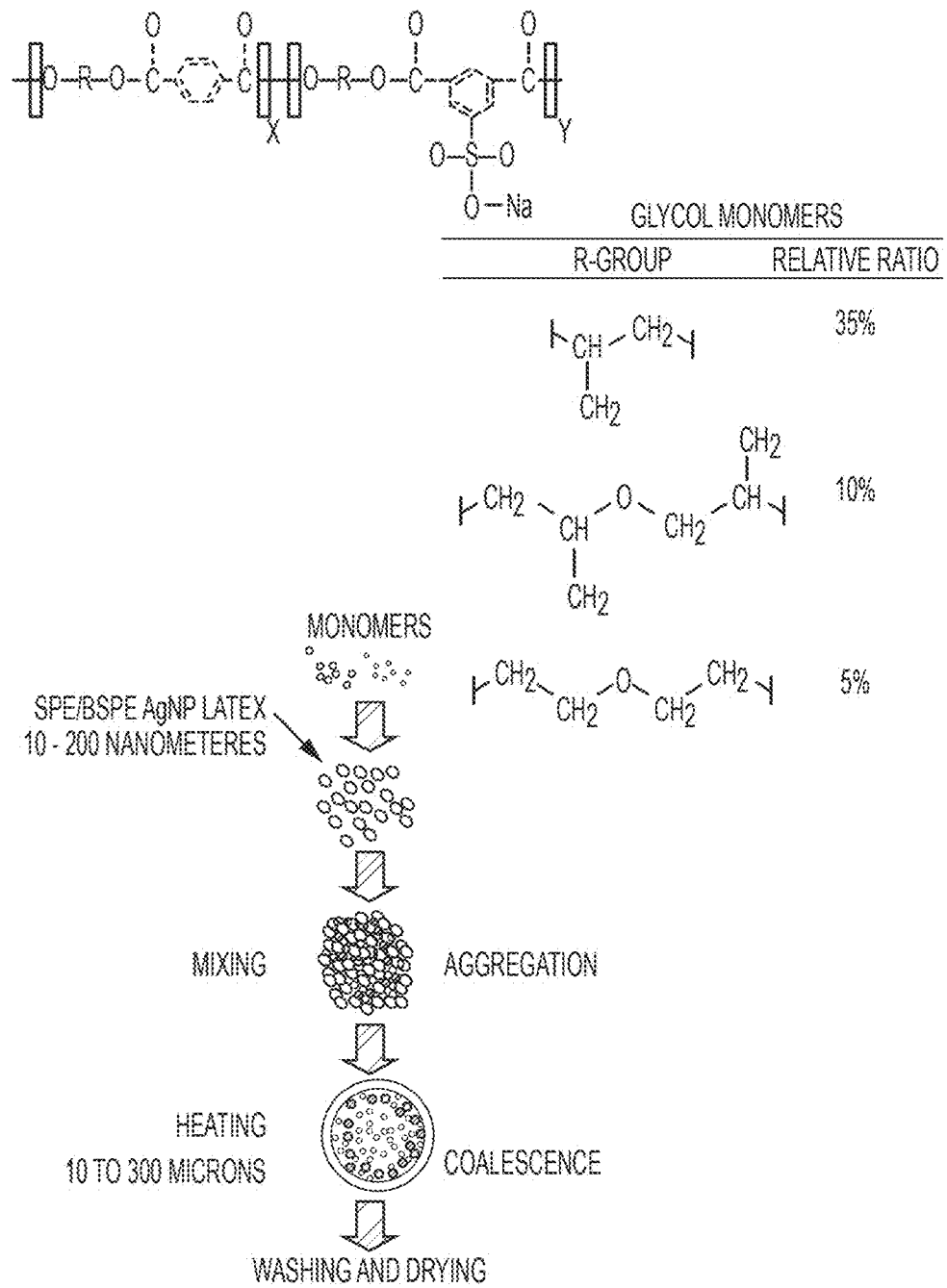
FIG. 2 shows a schematic of a possible mechanism of the preparation of dry particles for filament fabrication.

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges includes disclosure of all subranges included within the broader range (e.g., 1 to 5 discloses 1 to 4, 1 to 3, 1 to 2, 2 to 4, 2 to 3, . . . etc.).

The present disclosure provides a composite filament, more specifically, a sulfonated polyester polymeric composite filament containing silver nanoparticles (AgNPs), for use in Fused Deposition Modelling (FDM) application.

The class of AgNP polymer composites is more suitable for antibacterial applications compared to ionic and bulk silver, because silver salts may release silver too quickly and uncontrollably while bulk silver is very inefficient in releasing active silver species. AgNPs are known for their antibacterial properties; however the exact mechanism of antibacterial activity using AgNPs is poorly understood. The AgNPs may interact with the cell wall of the bacteria, consequently destabilizing the plasma-membrane potential and reducing the levels of intracellular adenosine triphosphate (ATP) resulting in bacterial cell death. Alternatively, AgNPs might play a role in the formation of reactive oxygen species (ROS) which is responsible for the cytotoxicity of bacteria cells in presence of AgNPs. "Potential Theranostics Application of Bio-Synthesized Silver Nanoparticles (4-in-1 System)," Theranostics 2014; 4(3):316-335. Furthermore, AgNPs have been reported to take part in chemical reduction-oxidation reactions as a catalyst by facilitating electron transfer between an electron donor and electron acceptor. "Micelle bound redox dye marker for nanogram level arsenic detection promoted by nanoparticles," New J. Chem., 2002, 26, 1081-1084.

The FDM composite filament of the present disclosure may be synthesized from sulfonated polyester-silver nanoparticles (SPE-AgNPs) where the SPE-AgNPs are aggregated from nano-sized to micron-sized then extruded into filaments. More specifically, a dry composite powder is first formed from the aggregation of self-dispersible sulfonated polyester (SPE) with embedded silver nanoparticles (AgNPs) that are simultaneously produced from silver nitrate with or without a reducing agent during the self-assembly of the sulfonated polyester resin particles in water. Subsequently, the dry composite powder is then processed into filaments from its powdered form, where the powdered form may optionally include additives and/or fillers.

The present disclosure pertain to polymeric filaments comprising a sulfonated polyester matrix and a plurality of silver nanoparticles may be prepared according to procedures disclosed in U.S. Pat. No. 6,866,807 U.S. Pat. No. 5,121,329, U.S. Pat. No. 6,730,252, U.S. Pat. No. 3,046,178, U.S. Pat. No. 6,923,634, U.S. Pat. No. 2,285,552, U.S. Pat. No. 4,012,557, U.S. Pat. No. 4,913,864, US Patent Publication 20040222561, and US Patent Publication 20150084222.

SPE-AgNPs

Certain embodiments herein provide methods of synthesizing silver nanoparticles (AgNPs) by reduction of silver (I) ion simultaneously during the self-assembly of sodio sulfonated polyester resin particles in water. The methods which employ water as the bulk solvent are environmentally friendly being free of organic solvents (or organic-free solvents). The methods are efficient requiring minimal time to prepare the polymer metal nanocomposites. Without being bound by theory it is postulated that silver ions are trapped within the polymer matrix during the self-assembly of the sodio sulfonated polyester while simultaneously being reduced to AgNPs. The sulfonated polyester-silver nanoparticles (SPE-AgNPs) are simultaneously synthesized during the self-assembly or dispersing of polymer in water as indicated in FIG. 1. Thus, the sodio sulfonated polyester serves as both a carrier for the silver ions and an organic matrix for the in situ synthesis of silver nanocomposites. The reducing agent is added during the self-assembly of sodio sulfonated polyester to reduce silver nitrate into silver nanoparticles (AgNPs) resulting in well dispersed particles. The polyester matrix plays an important role as it is postulated to inhibit the agglomeration of AgNPs. Meanwhile, the porosity of the sulfonated polyester allows the silver ions to diffuse and/or absorb throughout the polymer matrix allowing unhindered interaction with the sulfonate functional groups of the polyester. The reducing agent employed in the reduction of silver ion also freely diffuses throughout the polyester matrix and promotes the formation of well-dispersed AgNPs on the surface and interior of the polyester particles. Advantageously, the process minimizes nanoparticle agglomeration that plagues conventional methods with pre-formed nanoparticles. The sulfonated polymer matrix has an important role in keeping the AgNPs dispersed as well as maintaining overall chemical and mechanical stability of the composite.

Silver has many useful properties, including its antibacterial, antimicrobial, antifungal, antiviral properties. These novel properties of the silver nanocomposite materials disclosed herein make them useful in applications such as electronics components, optical detectors, chemical and biochemical sensors and similar devices. The ability to miniaturize any of these materials is a substantial benefit of the silver nanocomposite materials described herein.

The sulfonated polyester resins disclosed herein have been selected to have a hydrophobic backbone while presenting hydrophilic sulfonate groups attached along the chain. Without being bound by theory, when placed in water and heated, the hydrophobic portions may interact with each other to form a hydrophobic core with the hydrophilic sulfonate groups facing the surrounding water resulting in the sulfonated polyester self-assembling into a higher order, spherical nanoparticle without the requirement of additional reagents. Thus, there is a higher order involving the amphiphilic polyester, in which the hydrophobic backbone, which is insoluble in water, and the water-soluble hydrophilic sulfonate groups, operate as macrosurfactants. This results in self-association, self-assembly, self-dispersible nanoparticles in aqueous medium to yield micelle-like aggregates. The formation of silver nanoparticles within and surrounding the micelles is a secondary occurrence upon addition of silver nitrate and reducing agent.

In embodiments, there are provided composites comprising a sulfonated polyester matrix, and a plurality of silver nanoparticles dispersed within the matrix.

In embodiments, the sulfonated polyester matrix is a branched polymer. In embodiments, the sulfonated polyester matrix is a linear polymer. The selection of branched or linear polymer may depend on, inter alia, the downstream application of the composite product. Linear polymers can be used to create strands of fibers or form a strong mesh-like structure. Branched polymers may be useful to confer thermoplastic properties on the resultant composite material.

In embodiments, sulfonated polyesters of the present disclosure can be a homopolymer of one ester monomer or a copolymer of two or more ester monomers. Examples of suitable sulfonated polyesters include those disclosed in U.S. Pat. Nos. 5,348,832, 5,593,807, 5,604,076, 5,648,193, 5,658,704, 5,660,965, 5,840,462, 5,853,944, 5,916,725, 5,919,595, 5,945,245, 6,054,240, 6,017,671, 6,020,101, 6,140,003, 6,210,853 and 6,143,457, the disclosures of each of which are totally incorporated herein by reference.

In embodiments, sulfonated polyesters of the present disclosure can be hydrogen or a salt of a random sulfonated polyester, including salts (such as metal salts, including aluminum salts, salts of alkali metals such as sodium, lithium, and potassium, salts of alkaline earth metals such as beryllium, magnesium, calcium, and barium, metal salts of transition metals, such as vanadium, iron, cobalt, copper, and the like, as well as mixtures thereof) of poly(1,2-propylene-5-sulfoisophthalate), poly(neopentylene-5-sulfoisophthalate), poly(diethylene-5-sulfoisophthalate), copoly(1,2-propylene-5-sulfoisophthalate)-copoly-(1,2-propylene-terephthalate phthalate), copoly(1,2-propylene-diethylene-5-sulfoisophthalate)-copoly-(1,2-propylene-diethylene-terephthalate phthalate), copoly(ethylene-neopentylene-5-sulfoisophthalate)-copoly-(ethylene-neopentylene-terephthalate-phthalate), copoly(propoxylated bisphenol A)-copoly-(propoxylated bisphenol A-5-sulfoisophthalate), copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly-(propylene-diethylene-5-sulfoisophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), copoly(ethoxylated bisphenol-A-maleate)-copoly(ethoxylated bisphenol-A-5-sulfo-isophthalate), copoly(propylene-diethylene terephthalate)-copoly(propylene-5-sulfoisophthalate), copoly(neopentyl-terephthalate)-copoly-(neopentyl-5-sulfoisophthalate), and the like, as well as mixtures thereof.

In general, the sulfonated polyesters may have the following general structure, or random copolymers thereof in which the n and p segments are separated.

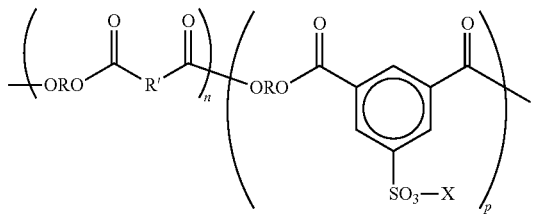

wherein R is an alkylene of, for example, from 2 to about 25 carbon atoms such as ethylene, propylene, butylene, oxyalkylene diethyleneoxide, and the like; R' is an arylene of, for example, from about 6 to about 36 carbon atoms, such as a benzylene, bisphenylene, bis(alkyloxy) bisphenolene, and the like; and p and n represent the number of randomly repeating segments, such as for example from about 10 to about 100,000.

Examples of the sulfonated polyesters further include those disclosed in U.S. Pat. No. 7,312,011 which is incorporated herein by reference in its entirety. Specific examples of amorphous alkali sulfonated polyester based resins include, but are not limited to, copoly(ethylene-terephthalate)-copoly-(ethylene-5-sulfo-isophthalate), copoly(propylene-terephthalate)-copoly(propylene-5-sulfo-isophthalate), copoly(diethylene-terephthalate)-copoly(diethylene-5-sulfo-isophthalate), copoly(propylene-diethylene-terephthalate)-copoly(propylene-diethylene-5-sulfo-isophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), and copoly(ethoxylated bisphenol-A-maleate)-copoly(ethoxylated bisphenol-A-5-sulfo-isophthalate), and wherein the alkali metal is, for example, a sodium, lithium or potassium ion. Examples of crystalline alkali sulfonated polyester based resins alkali copoly(5-sulfoisophthaloyl)-co-poly(ethylene-adipate), alkali copoly(5-sulfoisophthaloyl)-copoly(propylene-adipate), alkali copoly(5-sulfoisophthaloyl)-copoly(butylene-adipate), alkali copoly(5-sulfo-isophthaloyl)-copoly(pentylene-adipate), and alkali copoly(5-sulfo-iosphthaloyl)-copoly(octylene-adipate), alkali copoly(5-sulfo-isophthaloyl)-copoly(ethylene-adipate), alkali copoly(5-sulfo-isophthaloyl)-copoly (propylene-adipate), alkali copoly(5-sulfo-isophthaloyl)-co-poly (butylene-adipate), alkali copoly(5-sulfo-isophthaloyl)-copoly(pentylene-adipate), alkali copoly(5-sulfo-isophthaloyl)-copoly(hexylene-adipate), alkali copoly(5-sulfo-isophthaloyl)-copoly(octylene-adipate), alkali copoly (5-sulfoisophthaloyl)-copoly(ethylene-succinate), alkali copoly(5-sulfoisophthaloyl-copoly(butylene-succinate), alkali copoly(5-sulfoisophthaloyl)-copoly(hexylene-succinate), alkali copoly(5-sulfoisophthaloyl)-copoly(octylene-succinate), alkali copoly(5-sulfo-isophthaloyl)-copoly(ethylene-sebacate), alkali copoly(5-sulfo-isophthaloyl)-copoly (propylene-sebacate), alkali copoly(5-sulfo-isophthaloyl)-copoly(butylene-sebacate), alkali copoly(5-sulfo-isophthaloyl)-copoly(pentylene-sebacate), alkali copoly(5-sulfo-isophthaloyl)-copoly(hexylene-sebacate), alkali copoly(5-sulfo-isophthaloyl)-copoly(octylene-sebacate), alkali copoly(5-sulfo-isophthaloyl)-copoly(ethylene-adipate), alkali copoly(5-sulfo-isophthaloyl)-copoly(propylene-adipate), alkali copoly(5-sulfo-iosphthaloyl)-copoly (butylene-adipate), alkali copoly(5-sulfo-isophthaloyl)-copoly(pentylene-adipate), alkali copoly(5-sulfo-isophthaloyl)copoly(hexylene-adipate), poly(octylene-adipate), and wherein the alkali is a metal such as sodium, lithium or potassium. In embodiments, the alkali metal is sodium.

The sulfonated polyesters suitable for use in the present disclosure must be able to be melt-processed into a filament of appropriate diameter for the rate of extrusion of the particular FDM apparatus.

The sulfonated polyesters suitable for use in the present disclosure may have a glass transition (Tg) temperature of from about 45° C. to about 95° C., or from about 52° C. to about 70° C., as measured by the Differential Scanning calorimeter. The sulfonated polyesters may have a number average molecular weight of from about 2,000 g per mole to about 150,000 g per mole, from about 3,000 g per mole to about 50,000 g per mole, or from about 6,000 g per mole to about 15,000 g per mole, as measured by the Gel Permeation Chromatograph. The sulfonated polyesters may have a weight average molecular weight of from about 3,000 g per mole to about 300,000 g per mole, from about 8,000 g per mole to about 90,000 g per mole, or from about 10,000 g per mole to about 60,000 g per mole, as measured by the Gel Permeation Chromatograph. The sulfonated polyesters may have a polydispersity of from about 1.6 to about 100, from about 2.0 to about 50, or from about 5.0 to about 30, as calculated by the ratio of the weight average to number average molecular weight.

The linear amorphous polyester resins are generally prepared by the polycondensation of an organic diol and a diacid or diester, at least one of which is sulfonated or a sulfonated difunctional monomer being included in the reaction, and a polycondensation catalyst. For the branched amorphous sulfonated polyester resin, the same materials may be used, with the further inclusion of a branching agent such as a multivalent polyacid or polyol.

Examples of diacid or diesters selected for the preparation of amorphous polyesters include dicarboxylic acids or diesters selected from the group consisting of terephthalic acid, phthalic acid, isophthalic acid, fumaric acid, maleic acid, itaconic acid, succinic acid, succinic anhydride, dodecylsuccinic acid, dodecylsuccinic anhydride, glutaric acid, glutaric anhydride, adipic acid, pimelic acid, suberic acid, azelic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and mixtures thereof. The organic diacid or diester are selected, for example, from about 45 to about 52 mole percent of the resin. Examples of diols utilized in generating the amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hyroxyethyl)-bisphenol A, bis(2-hyroxypropyl)-bisphenol A, 1,4-cyclohexanedimethanol, 1,3-cyclohexanedimethanol, xylenedimethanol, cyclohexanediol, diethylene glycol, bis(2-hydroxyethyl) oxide, dipropylene glycol, dibutylene, and mixtures thereof. The amount of organic diol selected can vary, and more specifically, is, for example, from about 45 to about 52 mole percent of the resin.

Alkali sulfonated difunctional monomer examples, wherein the alkali is lithium, sodium, or potassium, include dimethyl-5-sulfo-isophthalate, dialkyl-5-sulfo-isophthalate-4-sulfo-1,8-naphthalic anhydride, 4-sulfo-phthalic acid, 4-sulfophenyl-3,5-dicarbomethoxybenzene, 6-sulfo-2-naphthyl-3,5-dicarbomethoxybenzene, sulfo-terephthalic acid, dimethyl-sulfo-terephthalate, dialkyl-sulfo-terephthalate, sulfo-ethanediol, 2-sulfo-propanediol, 2-sulfo-butanediol, 3-sulfo-pentanediol, 2-sulfo-hexanediol, 3-sulfo-2-methylpentanediol, N,N-bis(2-hydroxyethyl)-2-aminoethane sulfonate, 2-sulfo-3,3-dimethylpent-anediol, sulfo-p-hydroxybenzoic acid, mixtures thereto, and the like. Effective difunctional monomer amounts of, for example, from about 0.1 to about 2 weight percent of the resin can be selected.

Branching agents for use in forming the branched amorphous sulfonated polyester include, for example, a multivalent polyacid such as 1,2,4-benzene-tricarboxylic acid, 1,2,4-cyclohexanetricarboxylic acid, 2,5,7-naphthalenetricarboxylic acid, 1,2,4-naphthalenetricarboxylic acid, 1,2,5-hexanetricarboxylic acid, 1,3-dicarboxyl-2-methyl-2-methylene-carboxylpropane, tetra(methylene-carboxyl)methane, and 1,2,7,8-octanetetracarboxylic acid, acid anhydrides thereof, and lower alkyl esters thereof, 1 to about 6 carbon atoms; a multivalent polyol such as sorbitol, 1,2,3,6-hexanetetrol, 1,4-sorbitane, pentaerythritol, dipentaerythritol, tripentaerythritol, sucrose, 1,2,4-butanetriol, 1,2,5-pentatriol, glycerol, 2-methylpropanetriol, 2-methyl-1,2,4-butanetriol, trimethylolethane, trimethylolpropane, 1,3,5-trihydroxymethylbenzene, mixtures thereof, and the like. The branching agent amount selected is, for example, from about 0.1 to about 5 mole percent of the resin.

Polycondensation catalyst examples for amorphous polyesters include tetraalkyl titanates, dialkyltin oxide such as dibutyltin oxide, tetraalkyltin such as dibutyltin dilaurate, dialkyltin oxide hydroxide such as butyltin oxide hydroxide, aluminum alkoxides, alkyl zinc, dialkyl zinc, zinc oxide, stannous oxide, or mixtures thereof; and which catalysts are selected in amounts of, for example, from about 0.01 mole percent to about 5 mole percent based on the starting diacid or diester used to generate the polyester resin.

In particular embodiments, the sulfonated polyester matrix comprises a polyol monomer unit selected from the group consisting of trimethylolpropane, 1,2-propanediol, diethylene glycol, and combinations thereof.

In particular embodiments, the sulfonated polyester matrix comprises a diacid monomer unit selected from the group consisting of terephthalic acid, sulfonated isophthalic acid, and combinations thereof.

In embodiments, the sulfonated polyester-silver core nanoparticles may have a particle size in a range from about 5 nm to about 500 nm, or about 10 to about 200 nm, or about 20 to about 100 nm. A core particle size of less than 100 nm may be useful for reinforcement of polymer matrices without disturbing transparency and other properties of coatings. Tsavalas, J. G. et al. J. Appl. Polym. Sci., 87:1825-1836 (2003). As used herein, references to "particle size" will generally refer to $D_{50}$ mass-median-diameter (MMD) or the log-normal distribution mass median diameter. The MMD is considered to be the average particle diameter by mass.

In embodiments, the silver nanoparticles may include solely elemental silver or may be a silver composite, including composites with other metals. Such metal-silver composite may include either or both of (i) one or more other metals and (ii) one or more non-metals. Suitable other metals include for example Al, Au, Pt, Pd, Cu, Co, Cr, In, and Ni, particularly the transition metals for example Au, Pt, Pd, Cu, Cr, Ni, and mixtures thereof. Exemplary metal composites are Au—Ag, Ag—Cu, Au—Ag—Cu, and Au—Ag—Pd. Suitable non-metals in the metal composite include for example Si, C, and Ge. The various components of the silver composite may be present in an amount ranging for example from about 0.01% to about 99.9% by weight, particularly from about 10% to about 90% by weight. In embodiments, the silver composite is a metal alloy composed of silver and one, two or more other metals, with silver comprising for example at least about 20% of the nanoparticles by weight, particularly greater than about 50% of the nanoparticles by weight. Unless otherwise noted, the weight percentages recited herein for the components of the silver-containing nanoparticles do not include the stabilizer.

Silver nanoparticles composed of a silver composite can be made for example by using a mixture of (i) a silver compound (or compounds, especially silver (I) ion-containing compounds) and (ii) another metal salt (or salts) or another non-metal (or non-metals) during the reduction step.

In embodiments, the silver nanoparticles have a particle size in a range from about 2 to about 50 nm, or about 10 to about 50 nm or about 20 to about 50 nm. Silver nanoparticles of diameter less than 100 nm absorb light primarily below 500 nm. This property is useful as it allows the AgNPs to be used in combination with fluorescence emission detection since most fluorophores emit at a wavelength above 500 nm, thus minimizing quenching of the signal.

In embodiments, the sulfonated polyester-silver core nanoparticles may further comprise nanostructured materials, such as, without limitation, carbon nanotubes (CNTs, including single-walled, double-walled, and multi-walled), graphene sheet, nanoribbons, nano-onions, hollow nanoshell metals, nano-wires and the like. In embodiments, CNTs may be added in amounts that enhance electrical and thermal conductivity.

A shell polymer may be disposed over the sulfonated polyester-silver core nanoparticles. In embodiments, the shell polymer disposed about the sulfonated polyester-silver core nanoparticles comprises a styrene monomer, including substituted or unsubstituted styrenes. In embodiments, the shell polymer further comprises at least one vinyl monomer selected from the group consisting of methyl acrylate, ethyl acrylate, butyl acrylate, isobutyl acrylate, dodecyl acrylate, n-octyl acrylate, 2-ethylhexyl acrylate, 2-chloroethyl acrylate, phenyl acrylate, β-carboxyethyl acrylate, methyl α-chloro acrylate, methyl methacrylate, ethyl methacrylate, butyl methacrylate, butadiene, isoprene, methacrylonitrile, acrylonitrile, methyl vinyl ether, vinyl isobutyl ether, vinyl ethyl ether, vinyl acetate, vinyl propionate, vinyl benzoate, vinyl butyrate, vinyl methyl ketone, vinyl hexyl ketone, and methyl isopropenyl ketone, vinylidene chloride, vinylidene chloro fluoride, N-vinylindole, N-vinyl pyrrolidene, acrylic acid, methacrylic acid, acrylamide, methacrylamide, vinyl pyridine, vinyl pyrrolidone, vinyl N-methylpyridinium chloride, vinyl naphthalene, p-chlorostyrene, vinyl chloride, vinyl fluoride, ethylene, propylene, butylene, and isobutylene.

In embodiments, the shell polymer has a thickness from about 0.5 nm to about 100 nm, or from about 1.0 nm to about 50 nm, or from about 1.5 nm to about 20 nm.

In embodiments, the shell polymer confers to the sulfonated polyester-silver core nanoparticles one or more properties selected from the group consisting of (a) methanol resistance, (b) resistance to thermal degradation, and (c) acid/base resistance. With respect to methanol resistance, it is postulated that the polymer shell protects the core sulfonated polyester/AgNP composite from gelation. In embodiments, no more than about 10% material dissolves when, for example, a styrene shell is used.

With respect to resistance to thermal degradation, polymer shell-protected composites show only about 50% degradation at 400° C., while uncoated SPE-AgNP composites show about 80% decomposition at 400° C. The thermal stability of the styrene-coated composites, in particular, appears to be more complex than that of polystyrene alone. The first major mass loss of the styrene-coated composites starts around 300° C. (30.65%) but becomes more stable and degrades much slower than uncoated samples and polystyrene control.

With respect to acid/base resistance, addition of a polymer shell, such as styrene, to the sulfonated polyester-silver core nanoparticles may provide an improvement under basic conditions by 20 to 30%. Finally, a polymer shell, such as polystyrene, around the SPE/AgNp core provides substantially improved rigidity and strength of the organic/inorganic hybrid composite core materials.

Composite Filaments Synthesized from Sulfonated Polyester-Silver Nanoparticles SPE-AgNPs Composite powders as described herein are first prepared from the sulfonated polyester-silver nanoparticles (SPE-AgNPs), and then the composite powders are converted to composite filaments by filament fabrication.

The sulfonated polyester-silver nanoparticles (SPE-AgNPs) described herein can be produced by a method comprising heating a sulfonated polyester resin in an organic-free solvent, adding a solution of silver (I) ion to the heated resin in the organic-free solvent to form a mixture, adding a solution of a reducing agent to the mixture, thereby forming an emulsion of composite particles comprising a sulfonated polyester matrix and a plurality of silver nanoparticles disposed within the sulfonated polyester matrix. The term "organic-free solvent" refers to media that does not contain any organic solvent, an aqueous media such as water is considered to be an organic-free solvent. In embodiments, heating is conducted at a temperature from about 65° C. to about 90° C. Temperatures in this range are appropriate for both the initial dissolution of the polymer resin and subsequent reduction in the presence of silver ion. In embodiments, a source of silver (I) ion is selected from silver nitrate, silver sulfonate, silver fluoride, silver perchlorate, silver lactate, silver tetrafluoroborate, silver oxide, silver acetate. Silver nitrate is a common silver ion precursor for the synthesis of AgNPs. In embodiments, the reducing agent is selected from ascorbic acid, trisodium citrate, glucose, galactose, maltose, lactose, gallic acid, rosmarinic acid, caffeic acid, tannic acid, dihydrocaffeic acid, quercetin, sodium borohydride, potassium borohydride, hydrazine hydrate, sodium hypophosphite, hydroxylamine hydrochloride. In embodiments, reducing agents for the synthesis of AgNPs may include sodium borohydride or sodium citrate. Selection of appropriate reducing agent may provide access to desirable nanoparticle morphologies. For example, ascorbic acid was observed to provide silver nanoplate forms during a study directed to quantitation of vitamin C tablets. Rashid et al. *J. Pharm. Sci.* 12(1):29-33 (2013).

Composite powders may be prepared by conventional (ground and classification) or chemical (emulsion aggregation) means. U.S. Pat. Nos. 5,111,998, 5,147,753, 5,272,034, and 5,393,630 disclose conventional toner manufacturing processes are incorporated in their entirety by reference herein.

Figure 3:
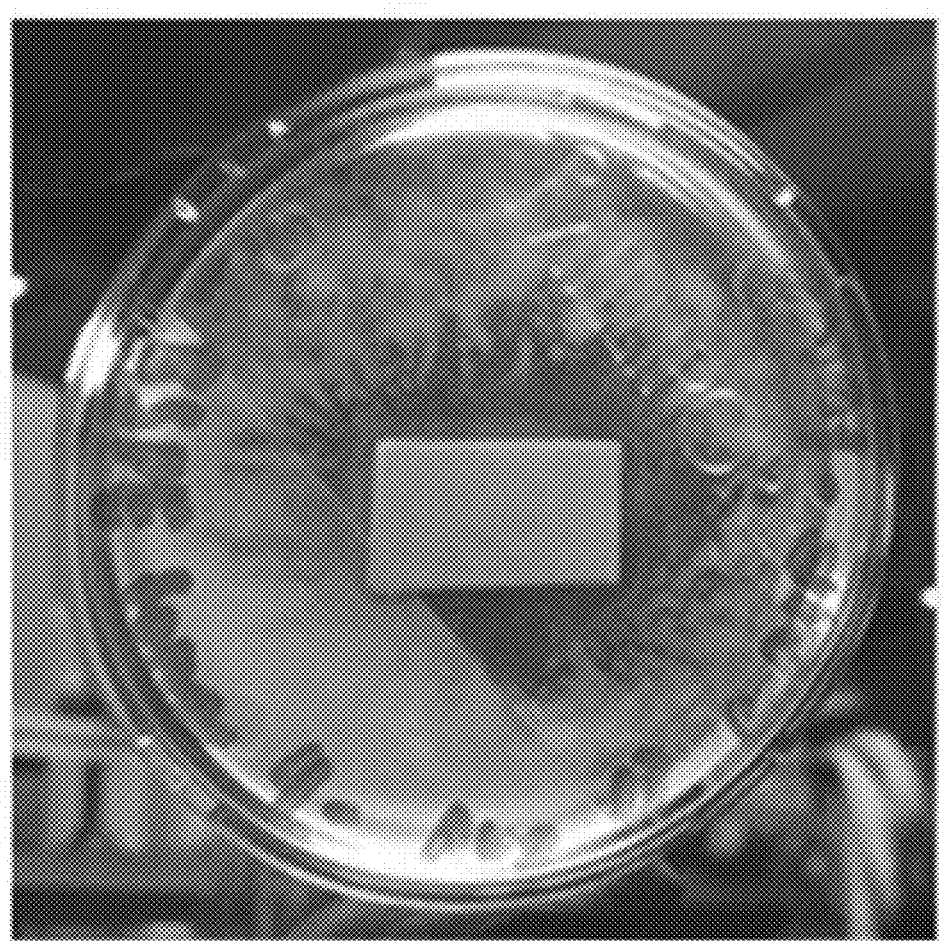
FIG. 3 is a grayscale image showing BSPE-AgNP antibacterial particles according to an embodiment of the disclosure (Example 3) fused onto glass microfiber membrane.

Composite powders may be prepared by emulsion aggregation means. The method to prepare the microparticles from polymeric coated sulfonated polyester-silver nanoparticles SPE-AgNPs is similar to the process known to generate toner particles (emulsion aggregation or EA). Particles of narrow size distribution and controllable particle size can be achieved with the aid of aggregating agents such as zinc acetate, magnesium chloride salts, aluminum sulfate and polyaluminum chloride (PAC). The particle morphology can be controlled via temperature, time, and stirring to provide particles that range from an irregularly shaped or an imperfect spherical to a near or perfect spherical. Any suitable emulsion aggregation procedure may be used in forming the emulsion aggregation composite particles without restriction. FIG. 3 shows an emulsion aggregation process for preparing dry particles for Fused Deposition Modelling (FDM) according to certain embodiments of the present disclosure. These procedures typically include the process steps of aggregating an emulsion of particles comprising a sulfonated polyester matrix and a plurality of silver nanoparticles disposed within the sulfonated polyester matrix, and one or more additional optional additives to form aggregated particles, subsequently coalescing the aggregated particles, and then recovering, optionally washing and optionally drying the obtained emulsion aggregation particles. However, in embodiments, the process is modified by the addition of a coalescent agent (or coalescence aid agent) prior to the coalescence. This addition of the coalescent agent provides toner particles having improved spheroidization, and allows the coalescence to be conducted in a shorter time, at a lower process temperature, or both. In embodiments, prior to the aggregation step, water is added to the SPE-AgNPs to form a slurry. In embodiments, the addition of water affords a total solid content based on the total weight of the slurry of from about 1% to about 40%, from about 5% to about 20%, or from about 10% to about 50%. The aggregating step includes heating the slurry to a temperature of from about 30° C. to about 80° C., from about 40° C. to about 70° C., or from about 50° C. to about 68° C. The duration of the aggregation step may be from about 1 minute to about 8 hours, from about 30 minutes to about 6 hour, or from about 60 minutes to about 4 hours. The coalescing step includes heating the aggregated particles to a temperature of from about 30° C. to about 95° C., from about 40° C. to about 95° C., or from about 60° C. to about 90° C. The duration of the coalescing step may be from about 1 minute to about 6 hours, from about 30 minutes to about 4 hour, or from about 60 minutes to about 3 hours.

Examples of suitable coalescent agents include, but are not limited to, benzoic acid alkyl esters, ester-alcohols, glycol-ether type solvents, long-chain aliphatic alcohols, aromatic alcohols, mixtures thereof, and the like. Examples of benzoic acid alkyl esters include benzoic acid alkyl esters where the alkyl group, which can be straight or branched, substituted or unsubstituted, has from about 2 to about 30 carbon atoms, such as decyl or isodecyl benzoate, nonyl or isononyl benzoate, octyl or isooctyl benzoate, 2-ethylhexyl benzoate, tridecyl or isotridecyl benzoate, 3,7-dimethyloctyl benzoate, 3,5,5-trimethylhexyl benzoate, mixtures thereof, and the like. Specific commercial examples of such benzoic acid alkyl esters include VELTA® 262 (isodecyl benzoate) and VELTA® 368 (2-ethylhexyl benzoate), available from Vlesicol Chemical Corporation. Examples of ester-alcohols include hydroxyalkyl esters of alkanoic acids where the alkyls group, which can be straight or branched, substituted or unsubstituted, independently have from about 2 to about 30 carbon atoms, such as 2,2,4-trimethylpentane-1,3-diol monoisobutyrate. Specific commercial examples of such ester-alcohols include TEXANOL® (2,2,4-trimethylpentane-1,3-diol monoisobutyrate) available from Eastman Chemical Company. Examples of glycol-ether type solvents include diethylene glycol monomethylether acetate, diethylene glycol monobutylether acetate, butyl carbitol acetate (BCA), and the like. Examples of long-chain aliphatic alcohols include those where the alkyl group is from about 5 to about 20 carbon atoms, such as ethylhexanol, octanol, dodecanol, and the like. Examples of aromatic alcohols include benzyl alcohol, and the like.

In embodiments, the coalescent agent (or coalescence aid agent) evaporates during later stages of the emulsion aggregation process or during coalescence, such as during the heating step that is generally near or above the glass transition temperature of the sulfonated polyester resin. The final composite powders are thus free of, or essentially or substantially free of, any remaining coalescent agent. To the extent that any remaining coalescent agent may be present in the final powder composites, the amount of remaining coalescent agent is such that it does not affect any properties or performance of the composite powders.

The coalescent agent can be added prior to the coalescence in any desired or suitable amount. For example, the coalescent agent can be added in an amount of from about 0.01 to about 10 percent by weight, based on the solids content in the reaction medium. For example, the coalescent agent can be added in an amount of from about 0.05 or from about 20.0, from about 0.1 to about 10.0 percent by weight, or from about 0.5 to about 5.0 percent by weight, based on the solids content in the reaction medium. In embodiments, the coalescent agent can be added prior to or at any time between aggregation and coalescence or upfront before heating.

Optional additives such as waxes, pigments, ceramics, carbon fiber or nanotubes, and fillers may be included in the composite powder. These additives may be added prior to or during the aggregation step or upfront before heating. The amount of additives present in the composite powder may be from about 0% to about 30%, from about 0% to about 20%, or from about 0% to about 10% by weight of the total weight of the composite powder.

The composite powders may be then fabricated into filaments. The composite filament of the present disclosure may be manufactured using an extrusion process. The composite powders may be first loaded into a melt flow index (MFI) instrument (also referred to as an extrusion plastometer) and equilibrated at a temperature of from about 60° C. to about 250° C., from about 60° C. to about 190° C., or from about 80° C. to about 150° C., for a period of time, such as from about 1 to about 90 minutes, from about 1 to about 60 minutes, from about 5 to about 45 minutes. After equilibration, the material obtained may be then extruded with a weight in a range of from about 1 kg to about 30 kg, from about 1 kg to about 20 kg, or from about 2 kg to about 10 kg, through a 0.5-5 mm diameter die to fabricate the FDM filament. In embodiments, the composite filament is in the form of a cylinder with a diameter of, for example, about 0.5 mm to about 5.0 mm, about 1.5 mm to about 3.0 mm, about 1.75 mm to about 3.0 mm. The length of the composite filament can be in any length, for example, for testing purposes, from about 2 ft to about 100 ft, from about 2 ft to about 50 ft, from about 5 ft to about 20 ft, and for commercial purposes, from about 50 ft to 2000 ft, from about 300 ft to about 1500 ft, or from about 400 ft to about 1300 ft.

The process of filament fabrication merely changes the physical appear of the composite and does not alter the material or content of the composite. Thus, the filament of the present disclosure comprises the same sulfonated polyester matrix and silver nanoparticles as described herein. In embodiments, the filament comprises the same sulfonated polyester-silver core nanoparticles as described herein. In embodiments, the filament comprises the same sulfonated polyester-silver core nanoparticles having a shell polymer disposed over as described herein.

In embodiments, a loading of silver nanoparticle is present in the composite filaments in a range from about 0.5 ppm to about 50,000 ppm, from about 5 ppm to about 5,000, from about 10 ppm to about 2,500, ppm, or from about 50 ppm to about 1,000 ppm. Loading concentrations of silver within this range can be used for antibacterial applications. Lower concentrations of silver might be sufficient for catalytic applications; concentrations of AgNPs as low as 1 ppm have been used. Ghosh, S. K. et al. *Langmuir.* 18(23):8756-8760 (2002).

In embodiments, methods disclosed herein may be particularly well-suited for making composites with relatively low solids content. Under such conditions, silver ion and reducing agent may readily diffuse through the polymer matrix. In the case of silver ion, such ready diffusion may improve uniformity of distribution of silver throughout the matrix.

In embodiments, there are provided articles comprising a plurality of composite filament as described herein, the composite filaments may comprise a core particle comprising a sulfonated polyester matrix and a plurality of silver nanoparticles dispersed throughout the matrix and a shell polymer disposed about the core particle.

The properties of the composite herein make them useful in various applications including, without limitation, electronics components, optical detectors, chemical and biochemical sensors and devices. The ability to miniaturize any of these materials is a major benefit of using the nanoscale composite structures herein. Other areas of interest that employ the composite powder herein include, without limitation, antibacterial applications, optical bi-stability, textiles, photoresponsivity, environmental, biological, medicine (membranes and separation devices), functional smart coatings, fuel and solar cells, and as catalysts.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

General Process: Composite preparation involves dispersing a branched sodio sulfonated polyester (BSPE) in water at about 90° C., followed by addition of a silver nitrate solution and lastly a mild reducing agent such as trisodium citrate or ascorbic acid is added. The reduction of Ag(I) to Ag(0) occurs after the addition of Ag(I) salt to the BSPE and is facilitated by the reducing agent. AgNP-BSPE systems that are synthesized via the trisodium citrate reductant route can also utilize the citrate cap for further applications such as biosensors where the citrate ligand is employed for analyte binding for quantitative or qualitative analysis of analyte concentration in a sample.

Example 1

This example describes the preparation of a branched sodio sulfonated amorphous polyesters (BSPE) according to embodiments of the present disclosure A branched amorphous sulfonated polyester resin comprised of 0.425 mole equivalent of terephthalate, 0.080 mole equivalent of sodium 5-sulfoisophthalic acid, 0.4501 mole equivalent of 1,2-propanediol, and 0.050 mole equivalent of diethylene glycol, was prepared as follows. In a one-liter Parr reactor equipped with a heated bottom drain valve, high viscosity double turbine agitator, and distillation receiver with a cold water condenser was charged 388 grams of dimethylterephthalate, 104.6 grams of sodium 5-sulfoisophthalic acid, 322.6 grams of 1,2-propanediol (1 mole excess of glycols), 48.98 grams of diethylene glycol, (1 mole excess of glycols), trimethylolpropane (5 grams) and 0.8 grams of butyltin hydroxide oxide as the catalyst. The reactor was heated to 165° C. with stirring for 3 hours and then again heated to 190° C. over a one hour period, after which the pressure was slowly reduced from atmospheric pressure to about 260 Torr over a one hour period, and then reduced to 5 Torr over a two hour period. The pressure was then further reduced to about 1 Torr over a 30 minute period and the polymer was discharged through the bottom drain onto a container cooled with dry ice to yield 460 grams of sulfonated-polyester resin. The branched sulfonated-polyester resin had a glass transition temperature measured to be 54.5° C. (onset) and a softening point of 154° C.

Example 2

This Example shows the preparation of a branched sodio sulfonated amorphous polyesters-silver nanoparticles (BSPE-AgNPs) composite employing trisodium citrate as the reducing agent.

The reaction was carried out in a 3 necked, 500 mL round bottom flask equipped with an overhead stirrer, reflux condenser, thermocouple, hot plate, and nitrogen entrance (the condenser acted as the nitrogen exit). About 320 mL of DIW was charged into the flask at room temperature (22° C.). The heat was turned on set to 90° C. and nitrogen was run through the system (RPM=250). Once the temperature had stabilized, 100.0 g of solid BSPE was added to the system in a finely ground state (RPM=300). The solution became hazy and had a blue tinge. After 1.5 hours, 1.00 g $AgNO_3$ dissolved in 6.0 mL DIW was added dropwise to the solution at a rate of approx. 1 drop/second (RPM=387). The solution became slightly darker (brownish). After 10 minutes, 52.5 mL of 1% (w/w %) trisodium citrate solution (reducing agent) was added to the system dropwise at a rate of 1 drop per second. Upon complete addition, the solution was stirred at 90° C. for 2 hours (RPM=300). The solution was allowed to cool to room temperature (RPM=386). The final appearance of the emulsion was a light brown opaque solution. The solids content of the emulsion was 27.70%, the D50 was 69.6 nm, the pH was 4.77 and the zeta potential was −58.6 mV with a zeta deviation of 7.87 mV (breadth of distribution). The percentage of silver in the BSPE-AgNP composite was 0.28% w/w % or 0.0235 M. The amount of silver present in the particle was analyzed to be 2413 ppm by inductively coupled plasma (ICP) or 0.2413%.

Example 3

This Example shows the preparation of a branched sodio sulfonated amorphous polyesters-silver nanoparticles (BSPE-AgNPs) powder.

Into a 500-liter glass reactor was added 108.30 g of distilled water with 108.30 g BSPE-AgNP composite obtained from Example 2 to give a total solids of 13.85%. The reactor was fitted with a mechanical agitator and equipped with a single pitched blade impellor. The mixture was initially agitated at 250 rpm and heated via an electric heating mantle to 60° C. After 20 minutes, once the temperature of the solution reached 60° C., the rpm was increased to 400 and the zinc acetate solution (6 g of zinc acetate dihydrate in 100 g of DI water) addition was commenced. After 100 minutes all the zinc acetate solution was added and the temperature was increased by 2 degrees to 62° C. The particle size as measured by a Beckman Coulter Counter was found to be 15.0 microns with a geometric standard deviation (GSD) by volume to be 1.30 and GSD by number to be 1.25. The temperature was increased another degree to 63° C. and particle growth was monitored via the Coulter Counter. After 3 hours, the heat was turned off and the reactor contents were cooled to ambient temperature. The final particle size was 20.0 micron with a GSDv of 1.30 and a GSDn or 1.30. The particle was discharged from the reactor and the particles were filtered from the mother liquor and washed 2 times with distilled water (DIW). The final particle was redispersed into 200 mL of deionized water, frozen via shell-freezer and placed on a drier for 3 days to result in dry particles to be used for SLS additive manufacturing.

Example 4

This Example shows wet deposition of BSPE-AgNPs antibacterial particles to mimic glass microfiber membrane fusing.

A suspension of the particles prepared in Example 3 was prepared in water containing a small amount of Triton-X 100 surfactant. An amount of this suspension corresponding to 9.62 mg of particles was passed through a glass microfiber membrane through a cup with an exposed surface area of 9.62 cm². The retained particles and filter paper were dried at room temperature, then enveloped in Mylar film and passed through a GBC laminator set to 120° C.

Results after 3 days of incubation at 37° C. confirmed that the fused BSPE-AgNP particles showed no bacteria growth around the particle swatch or on the swatch itself. This zone of inhibition or "halo-effect" is quite large which means that the silver ions are easily released from the particles over a short period of time.

Example 5

This Example shows the fabrication of filaments.

The dried particles obtained from Example 4 were fed into the melt flow index (MFI) instrument (extrusion plastometer) and equilibrated at 90° C. for 6 minutes. The material was then extruded with a 17 kg weight through a 2 mm diameter die to fabricate the FDM filament for antibacterial testing. FIG. 4 is a photo image showing the BSPE-AgNPs antibacterial particles of Example 3 being fused onto a glass microfiber member.

Example 6

This Example shows the antibacterial testing of filaments

A 200 mm Pyrex® glass tube is filled with Bacto™ Tryptic Soy Broth and a filament from Example 4 is placed in the glass tube. The glass tube is sealed with a rubber stopper and being incubated at 37° C. and 90% humidity for 14 days. A control sample of BSPE filament (from Example 1) containing no AgNPs is also treated to the same incubation procedure. After the incubation period, the tubes are visually analyzed for turbidity. Prior to any filament incubation, the soy broth or TSB is transparent. Once the TSB is exposed to bacteria or fungi, the organisms will turn the liquid turbid due to reproduction/multiplication of bacteria. Another indicator of bacterial growth is accumulation of precipitation that will settle to the bottom of the test tube. The filament made with the BSPE-AgNPs in Example 4 shows no signs of bacterial contamination while the non-AgNP containing BSPE show both turbidity and precipitation indicating a lack of antibacterial activity.

What is claimed is:

1. A composite filament for use in fused deposition modelling, comprising:
   a sulfonated polyester matrix; and
   a plurality of silver nanoparticles dispersed within the matrix,
   wherein the silver nanoparticle is present in the composite filament in a range from about 0.5 ppm to about 50,000 ppm;
   and further wherein the composite filament has a diameter of from about 0.5 mm to about 5 mm.

2. The composite filament of claim 1, wherein the sulfonated polyester has a glass transition (Tg) temperature of from about 45° C. to about 95° C.

3. The composite filament of claim 1, wherein the sulfonated polyester matrix comprises a branched polymer.

4. The composite filament of claim 1, wherein the sulfonated polyester matrix comprises a linear polymer.

5. The composite filament of claim 1, wherein the composite filament is in the form of a cylinder having a diameter of about 0.5 mm to about 5.0 mm.

6. The composite filament of claim 1, wherein the sulfonated polyester matrix comprises hydrogen or a salt of a random sulfonated polyester, wherein the sulfonated polyester is selected from poly(1,2-propylene-5-sulfoisophthalate), poly(neopentylene-5-sulfoisophthalate), poly(diethylene-5-sulfoisophthalate), copoly(1,2-propylene-5-sulfoisophthalate)-copoly-(1,2-propylene-terephthalate phthalate), copoly(1,2-propylene-diethylene-5-sulfoisophthalate)-copoly-(1,2-propylene-diethylene-terephthalate phthalate), copoly(ethylene-neopentylene-5-sulfoisophthalate)-copoly-(ethylene-neopentylene-terephthalate-phthalate), copoly(propoxylated bisphenol A)-copoly-(propoxylated bisphenol A-5-sulfoisophthalate), copoly(ethylene-terephthalate)-copoly-(ethylene-5-sulfoisophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly-(propylene-diethylene-5-sulfoisophthalate), copoly(propylene-butylene-terephthalate)-copoly(propylene-butylene-5-sulfoisophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), copoly(ethoxylated bisphenol-A-maleate)-copoly(ethoxylated bisphenol-A-5-sulfo-isophthalate), copoly(propylene-diethylene terephthalate)-copoly(propylene-5-sulfoisophthalate), copoly(neopentyl-terephthalate)-copoly-(neopentyl-5-sulfoisophthalate), and mixtures thereof.

7. The composite filament of claim 6, wherein the salt is selected from the group consisting of sodium, lithium and potassium.

8. The composite of claim 1, wherein the sulfonated polyester matrix comprises a polyol monomer unit selected from the group consisting of trimethylolpropane, 1,2-propanediol, diethylene glycol, and combinations thereof.

9. The composite of claim 1, wherein the sulfonated polyester matrix comprises a diacid monomer unit selected from the group consisting of terephthalic acid, sulfonated isophthalic acid, and combinations thereof.

10. A method of producing a composite filament, comprising:
    heating a sulfonated polyester resin in an organic-free solvent;
    adding a solution of silver (I) ion to the heated resin in the organic-free solvent to form a mixture;
    adding a solution of a reducing agent to the mixture, thereby forming an emulsion of particles comprising a sulfonated polyester matrix and a plurality of silver nanoparticles disposed within the sulfonated polyester matrix;
    aggregating the emulsion of particles to form aggregated particles;
    coalescing the aggregated particles to form coalesced particles;
    washing the coalesced particles, thereby forming a composite powder; and
    extruding the composite powder to produce the composite filament.

11. The method of claim 10, wherein the heating of the sulfonated polyester resin is conducted at a temperature from about 65° C. to about 90° C.

12. The method of claim 10, wherein the aggregating is conducted at a temperature of from about 30° C. to about 80° C.

13. The method of claim 10, wherein the coalescing is conducted at a temperature of from about 30° C. to about 95° C.

14. The method of claim 10, wherein a source of silver (I) ion is selected from silver nitrate, silver sulfonate, silver fluoride, silver perchlorate, silver lactate, silver tetrafluoroborate, silver oxide and silver acetate.

15. The method of claim 10, wherein the reducing agent is selected from ascorbic acid, trisodium citrate.

16. The method of claim 10, wherein the sulfonated polyester resin is a branched polymer.

17. The method of claim 10, wherein the sulfonated polyester resin is a linear polymer.

18. The method of claim 10, wherein the sulfonated polyester matrix comprises hydrogen or a salt of a random sulfonated polyester, wherein the sulfonated polyester is selected from poly(1,2-propylene-5-sulfoisophthalate), poly(neopentylene-5-sulfoisophthalate), poly(diethylene-5-sulfoisophthalate), copoly(1,2-propylene-5-sulfoisophthalate)-copoly-(1,2-propylene-terephthalate phthalate), copoly(1,2-propylene-diethylene-5-sulfoisophthalate)-copoly-(1,2-propylene-diethylene-terephthalate phthalate), copoly(ethylene-neopentylene-5-sulfoisophthalate)-copoly-(ethylene-neopentylene-terephthalate-phthalate), copoly(propoxylated bisphenol A)-copoly-(propoxylated bisphenol A-5-sulfoisophthalate), copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly-(propylene-diethylene-5-sulfoisophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), copoly(ethoxylated bisphenol-A-maleate)-copoly(ethoxylated bisphenol-A-5-sulfo-isophthalate), copoly(propylene-diethylene terephthalate)-copoly(propylene-5-sulfoisophthalate), copoly(neopentyl-terephthalate)-copoly-(neopentyl-5-sulfoisophthalate), and mixtures thereof.

19. An article comprising:
a composite filament comprising:
    a sulfonated polyester matrix; and
    a plurality of silver nanoparticles dispersed within the matrix;
wherein the silver nanoparticle is present in the composite filament in a range from about 0.5 ppm to about 50,000 ppm;
and further wherein the composite filament has a diameter of from about 0.5 mm to about 5 mm.

20. The article of claim 19, wherein the article is selected from the group consisting of a biochemical sensor, an optical detector, an antibacterial, a textile, a cosmetic, an electronic component, a fiber, and a cryogenic superconducting material.

* * * * *